United States Patent [19]
Schlipfenbacher et al.

[11] Patent Number: 5,160,486
[45] Date of Patent: Nov. 3, 1992

[54] TEST CARRIER UTILIZING REACTION OF TWO BIOAFFINE BINDING PARTNERS

[75] Inventors: Reiner Schlipfenbacher, Lampertheim; Dieter Mangold, Maxdorf; Rolf Lerch, Ilvesheim; Joachim Steinbiss, Lorsch, all of Fed. Rep. of Germany

[73] Assignee: Boehringer Mannheim GmbH, Mannheim, Fed. Rep. of Germany

[21] Appl. No.: 450,557

[22] Filed: Dec. 14, 1989

[30] Foreign Application Priority Data

Dec. 19, 1988 [DE] Fed. Rep. of Germany ....... 3842702

[51] Int. Cl.⁵ .................... G01N 21/77; C12M 1/40
[52] U.S. Cl. ........................................ 422/56; 422/58; 436/169; 435/288; 435/805
[58] Field of Search ............... 422/56, 58; 436/169; 435/288, 805

[56] References Cited

U.S. PATENT DOCUMENTS

| | | |
|---|---|---|
| 3,723,064 | 3/1973 | Liotta ................. 436/169 X |
| 4,189,304 | 2/1980 | Adams, Jr. et al. ........... 422/56 X |
| 4,446,232 | 5/1984 | Liotta ................. 422/56 X |
| 4,615,983 | 10/1986 | Koyama ............... 422/56 X |
| 4,868,108 | 9/1989 | Babar et al. ............. 422/56 X |
| 4,950,454 | 8/1990 | Masuda et al. ............ 422/56 |
| 4,956,275 | 9/1990 | Zuk et al. .............. 435/288 X |
| 4,966,856 | 10/1990 | Ito et al. ............... 422/58 X |
| 4,972,366 | 12/1990 | Sudo et al. .............. 422/56 X |
| 5,028,535 | 7/1991 | Buechler et al. ........... 436/501 X |

FOREIGN PATENT DOCUMENTS

| | | |
|---|---|---|
| 0201339 | 11/1986 | European Pat. Off. . |
| 0225054 | 6/1987 | European Pat. Off. . |
| 0271204 | 6/1988 | European Pat. Off. . |
| 0284232 | 9/1988 | European Pat. Off. . |
| 0303110 | 2/1989 | European Pat. Off. . |
| 8604683 | 8/1986 | PCT Int'l Appl. . |
| 8906791 | 7/1989 | PCT Int'l Appl. ........... 422/56 |

Primary Examiner—Robert J. Warden
Assistant Examiner—Stephanie Blythe
Attorney, Agent, or Firm—Felfe & Lynch

[57] ABSTRACT

Test carrier for analysis of a sample liquid with the help of a specific binding reaction of two bioaffine binding partners, one of which is contained in the sample and one in the reagent system of the test carrier, with several capillary-active test zones (11–16; 21–25) arranged substantially next to one another on a base layer (2). The test zones are in liquid contact with one another so that they form a liquid transport path (20, 30) along which a liquid flows, driven by capillary forces, from a start zone (11, 21), a reaction thereby taking place between the first binding partner and the reagent system containing the second reaction partner, which reaction leads to a labelled species characteristic for the desired analysis. A third binding partner specific for the first binding partner sets as capturing reagent which is so arranged in a zone of the liquid transport path (20, 30) and is so measured with regard to the amount used that it binds a part of the first binding partner and thereby removes it from the reaction leading to the characteristic labelled species. A process for the analysis of a liquid sample with the above test carrier is also provided.

18 Claims, 1 Drawing Sheet

TEST CARRIER UTILIZING REACTION OF TWO BIOAFFINE BINDING PARTNERS

BACKGROUND OF THE INVENTION

The present invention is concerned with a test carrier for the analytical investigation of a sample liquid by means of a specific binding reaction of two specific binding partners, one of which is contained in the sample and the other in the reagent system of the test carrier. The test carrier has several capillary-active test zones arranged substantially next to one another on a test layer, which are in liquid contact with one another so that they form a liquid transport path along which a liquid flows by capillary forces from a starting zone to an end zone, a reaction thereby taking place between the first binding partner and the reagent system containing the second binding partner which results in a labelled species characteristic for the desired analysis, the labelled specific species being detected in a detection zone.

For the qualitative and quantitative analytical determinations in the scope of the diagnosis of diseases, so-called carrier-bound tests have recently been increasingly used. In the case of these tests, reagents are embedded in appropriate layers of a solid test carrier which are brought into contact with the sample. The sample is usually a body fluid, such as blood or urine. However, it can also be a liquid obtained by a preceding test step.

Test carriers are known in various forms. The present invention is concerned with those test carriers in which capillary-active test zones, which usually consist of absorbent material layers, for example, papers, fleece or porous synthetic resin layers, are arranged next to one another on a base layer in such a manner that the liquid flows along the liquid path parallel to the base layer. Therefore, these test carriers can also be referred to as "test carriers with longitudinal transport".

Such test carrier constructions are especially advantageous for analysis processes which are based on a specific binding reaction of two bioaffine binding partners. Examples therefor are described in Federal Republic of Germany patent specification No. 34 45 816, to which U.S. Pat. No. 4,861,711 corresponds and in U.S. Pat. No. 4,361,537. Specific binding reactions in this sense are, in particular, immunological interactions, thus reactions between antigens or haptens, on the one hand, and antibodies on the other hand. However, other specific interactions can also be used, such as lectin-sugar or an active material-receptor interaction. In the following, without limitation of the generality, reference is made by way of example to immunological reactions.

Greatly varying test principles can be used which are described in the literature, for example in the two above-mentioned patent specifications.

In a first group of immunological tests, one of the front zones of the liquid transport path contains the first binding partner (analyte) in soluble, labelled form. A test zone provided in the further course of the liquid transport path contains the second binding partner in carrier-fixed form. The analyte from the sample and the labelled analyte from the test compete for the binding positions on the second binding partner. Therefore, such tests are referred to as competitive tests.

In the case of a second group of known immunological tests, one of the front zones of the liquid transport path contains the second binding partner in soluble and labelled form. Due to the specific binding reaction with the first binding partner, mobile and labelled complexes are formed.

In the further course of the test, a further binding partner can be present in carrier-fixed form which is specifically bindable with a binding site of the first or second binding partner not saturated by the complex formation, a sandwich thereby resulting of at least three binding partners. Therefore, such tests are also referred to as sandwich tests.

In the case of the so-called immunoenzymometric (IEMA) principle, the further course of the test contains the analytes in carrier-fixed form, the noncomplexed part of the second binding partner thereby being fixed. Only the complexes remain mobile and can be detected.

It is common to all immunological determinations that the analysis reaction, which inter alia includes a specific binding reaction between the two binding partners, leads to a labelled species characteristic for the desired analysis. In the case of the competitive test, this is the analyte which is bound or which remains free. In the case of the sandwich test, these are the bound sandwich complexes. In the case of the IEMA test, it is the complex which remains freely mobile.

More detailed explanations of the various known immunological test principles are not necessary because they can be found in the appropriate literature. Independently of the special course of the test, the present invention can be advantageously used but it is, nevertheless, specially directed towards test carriers which work according to IEMA principle.

Various immunological processes of determination also differ with regard to the label employed. The present invention is especially concerned with enzyme immune tests in which an enzyme label is used. The labelling enzyme is usually detected by the colour-forming reaction of a substrate of the labelling enzyme. The substrate can, depending upon the carrying out of the test, already be present in the detection zone or can be added thereto. In principle, the present invention can also be used for non-enzymatic processes in which, for example, a coloured material or a radioactive element is used for the labelling.

SUMMARY OF THE INVENTION

In order to make available an easily handled test carrier which is economic to produce and which is especially suitable for the evaluation of comparatively highly concentrated analytes, for which immunological test carriers were previously not available, the present invention provides a test carrier for the analytical investigation of a sample liquid with the help of a specific binding reaction of two binding partners, of which a first is contained in the sample and a second is contained in the reagent system of the test carrier. Several capillary-active test zones are arranged substantially next to one another on a base layer, which test zones are in liquid contact with one another so that they form a liquid transport path along which a liquid flows, driven by capillary forces, from a start zone. A reaction thereby takes place between the first binding partner and the reagent system containing the second binding partner, which reaction leads to a labelled species characteristic for the desired analysis. A specific third binding partner acting as capturing reagent for the first binding partner is so arranged in a zone of the liquid transport path and is so measured with regard to the amount used that it binds a part of the first binding partner and thereby removes it from the exchange action leading to the characteristic labelled species.

Immunological determinations are characterised by an extremely high sensitivity. This is an advantage for low concentrated analytes but endeavours have long since been made also to use the advantages of immunological determinations for higher concentrated analytes. The great sensitivity thereby proves to be a serious problem. Of course, it is possible manually to dilute the sample correspondingly. However, this requires a handling step which can only be carried out by trained laboratory personnel and which is time-consuming. Therefore, attempts have been made to reduce the sensitivity of the test process by laborious means. For example, binding partners are used in the test which display a reduced affinity towards the analyte or the stoichiometry between the labelled binding partner and the labelling enzyme is manipulated.

SUMMARY OF THE INVENTION

In comparison with these known, laborious processes, the present invention now provides a surprisingly simple way by providing a capturing reagent specific for the analyte. A reduction of the analyte concentration on the test carrier is thereby to some extent achieved without a separate previously provided dilution step being necessary. The carrier according to the present invention is advantageous for concentrations of above $10^{-8}$ mole/liter and especially of above $10^{-7}$ mole/liter.

A further proposal which represents a valuable supplementation of the above-mentioned measures but, nevertheless, also has an independent importance, relates to the starting zone, the construction of which is important for the handling and function of the test carriers, which is explained in more detail in the following.

In this regard, the present invention proposes, in the case of a test carrier of the initially mentioned type, the production of the starting zone from a non-swelling fibre fleece which contains a binder which is insoluble at ambient temperature.

Also in this regard, the present invention differs fundamentally from the prior art. Thus, in Federal Republic of Germany patent specification No. 34 45 816 and in European patent specification No. 0,052,328, it is stated that especially synthetic resin sponges or layers of hydrophilic materials are suitable which, on the basis of their swelling properties, have an especially high water take-up. It is thereby ensured that the starting zone, in the case of dipping into a sample liquid, takes up sufficient liquid in order to fill the whole of the liquid transport path of the test carrier, even when, after the dipping into the sample, no further liquid is supplied.

Surprisingly, we have found, in the scope of the present invention, that especially good results can be achieved with a comparatively hydrophobic material, which, referred to its inherent weight, has a smaller liquid take-up but is emptied to a high degree on the test carrier.

Quantitatively, this property can be expressed as liquid retention. In the scope of the present invention, this is determined by laying a sample of 25 cm² surface area on a sponge cloth which is considerably larger than the sample and is wetted through to saturation. The amount of water removed from the sponge is determined by weighing. The wet sample is laid on a round filter of the type 2668/8 of the firm Schleicher & Schüll, Dassel, Federal Republic of Germany, with a diameter of 158 mm. and removed after 2 minutes. The amount of water taken up by the round filter is again determined by weighing. The retention is determined as the percentage relationship of the amount of water remaining in the sample to the amount of water originally taken up. In this sense, materials are preferred which have a liquid retention of at most 25% for the sample liquid.

DETAILED DESCRIPTION OF THE PREFERRED EMBODIMENT

Figure 1:
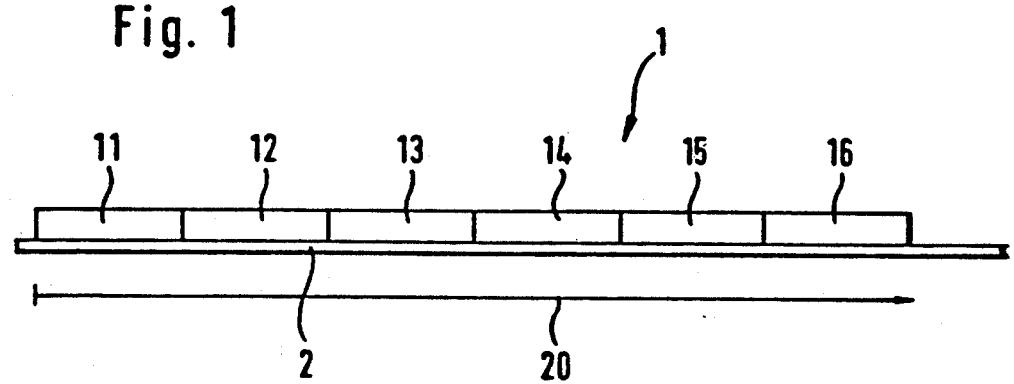
FIG. 1 is a schematic view illustrating the principle of the zone sequence in a test carrier.

FIG. 1 serves for the explanation of the various possible test principles and arrangements of the capturing reagent of the test carrier. Therefore, it omits constructional details and merely shows, in principle, a test carrier 1 with a base layer 2 on which are arranged next to one another, with their end faces abutting, test zones 11 to 16. The test zones preferably each consist of various absorbent materials (papers, fleece, porous synthetic resin layers and the like), the liquid contact on the abutting edges being achieved by a sufficiently close placing together of the layers. However, it can also be advantageous for the layers partly to overlap (cf. FIG. 2) or for several adjacent zones to be produced in one piece from the same material. In all, the test zones form a liquid transport path 20 which runs from the start zone 11 to the end zone 16.

In the case of the use of the test carrier, at first only the start zone 11 is contact with the sample liquid, preferably by appropriately dipping the test carrier into the sample liquid. Thereafter, the start zone gradually gives up its liquid content to the liquid transport path. The liquid chromatographs mainly driven by the capillary forces prevailing in the zones 11 to 16 up to the end zone 16. Details of the thereby important liquid transport properties of the zones are dealt with in more detail in connection with FIG. 2.

The start zone 11 is followed in the illustrated case by a sample application zone 12 and an auxiliary reagent zone 13. The function of the sample application zone 12 is explained in more detail hereinafter. The auxiliary reagent zone 13 contains a buffer in order to adjust the pH value of the sample to the requirements of the test. If desired, it can contain further auxiliary reagents, for example wetting agents and the like. In general, there can be present more or less zones than illustrated, depending upon the requirements of the test.

Depending upon the individual case of the immunological test principle to be used, immunological components of the reagent system are contained in the zones of the test carrier. Some examples are explained in the following.

In the case of a competitive test for the determination of an antigen Ag contained in the sample, the zone 14 can, for example, contain a conjugate AgE of the antigen with a labelling enzyme in soluble form. The zone 15 contains, as second binding partner, an antibody in carrier fixed form Ab1(f).

In the case of flow through of the sample, the AgE is dissolved. Ag and AgE compete for binding positions on the Ab1(f). When the liquid further flows into the end zone 16, a separation takes place between the AgE fixed in the zone 15 by binding on the Ab1(f) and the AgE remaining free, which flows further into the zone 16. The amount of AgE bound in the zone 15 is specific and characteristic for the analysis and can be detected there in that, for example, in a further process step, a colour-forming substrate is supplied to the enzyme and the colour formation in the zone 15 is observed. In this regard, the course of the test is conventional (cf., for example, U.S. Pat. No. 4,861,711.

As capturing reagent, there is present in the zone 13 a carrier-fixed third binding partner Ab2(f). It serves the purpose of fixing a part of the sample antigen before it passes into the zone 14 with the antigen conjugate. In this way, a certain part of the antigen (thus, generally expressed, the first binding partner) is removed from the analytical reaction leading to the labelled species.

As mentioned, the antibodies Ab1(f) and Ab2(f) must, in each case, be specifically bindable with the same antigen. The same antibody can preferably be employed.

In the case of a test carrier working according to the immunoenzymometric test principle (IEMA) for the determination of an antigen Ag contained in the sample, the zone 14 contains a soluble conjugate AbE of an antibody with a labelling enzyme (second binding partner), bind specifically with the antigen. The zone 15 contains the antigen in carrier-fixed form (Ag(f), further binding partner). In the case of the flowing through of the sample, the AbE is dissolved and forms complexes Ag-AbE with the Ag. Non-complexed AbE is bound in the zone 15 on to the Ag(f), whereas the Ag-AbE complexes remain free. When the liquid continues to flow into the zone 16, there takes place a separation of the bound AbE and of the freely mobile Ag-AbE complexes characteristic for the analysis. The latter can be detected in the zone 16, a colour-forming substrate of the labelling enzyme thereby advantageously being present in the zone 16. This part of the test is also known.

Whereas in the case of the competitive test, the detection takes place as described above preferably in the zone 15, i.e. in the zone with the fixed binding partner, AbL(f) in the case of the immunoenzymometric test, the zone 16 following the fixing zone 15 serves as the detection zone.

Immunoenzymometric tests are characterised by an especially high sensitivity and a simple handling. In the scope of the present invention, we have, surprisingly, shown that test carriers which work according to this principle can also be successfully used for the direct detection of comparatively highly dosed analytes (concentrations greater than 0.1 $\mu$mole/liter) without the advantages with regard to the ease of handling thereby being lost.

Again, a capturing reagent is provided which, just as in the case of the previously described competitive test principle, can be contained in the zone 13, i.e. in a zone of the test carrier placed before the conjugate zone, in soluble or carrier-fixed form.

Another variant is especially preferred in which the capturing reagent is present in soluble form, together with the conjugate, in the same zone (in the case of the example thus in zone 14). In this case, the antibody used as capturing reagent should have the same specificity of action as the antibody used in the conjugate. Therefore, there is especially suitable an identical monoclonal antibody but optionally also a polyclonal antibody with a very narrow epitope spectrum.

In the case of this variant of the present invention, the capturing reagent, which has no enzyme labelling, competes with the conjugate for the specific binding positions on the analyte. There is thereby achieved an essentially percentage "dilution", i.e. the portion of the analyte which is removed by the capturing reagent from the detection reaction corresponds approximately to the ratio between capturing reagent and conjugate.

The possibility of providing the capturing reagent in free form is not limited to the case in which it is provided in the same zone as the conjugate. In its complete generality, the present invention encompasses, on the contrary, also test carriers in which a soluble capturing reagent is contained in a suitable zone of the liquid transport path before the detection zone.

The amount of the capturing reagent is to be adjusted to the specific requirements. Theoretically, it must be smaller than the smallest amount of the analyte in the sample to be detected (limit of detection). In practice, however, it depends upon various factors. These include the affinity constant of the antibody used, details of the structure of the conjugate and the speed with which the liquid flows through the zone which contains the capturing reagent. Also of importance is the extent to which the binding of the sample antigen to the capturing reagent is complete. On the basis of theoretical considerations, one should have expected that this would include such considerable uncertainties that a considerable falsification of the measurement results are to be feared. However, in practice, we have, surprisingly, shown that the amount of capturing reagent can be empirically so determined that an immunological determination of highly concentrated parameters is possible with good accuracy.

Preferably, the absorbent layer material which forms the test zone with the capturing reagent is impregnated with an impregnation solution in which is contained the capturing reagent in a molar concentration which corresponds approximately to the desired limit of detection of the analytical determination. The concentration of the capturing reagent in the impregnation solution should be at least half as great as the desired limit of detection. In absolute figures, the concentration is at least $10^{-8}$ mole/liter and preferably at least $10^{-7}$ mole/liter.

The sample need not necessarily be applied to the starting zone. On the contrary, a special sample application zone 12 can be provided. This is, in particular, advantageous when an additional sample dilution is to be achieved.

The sample is thereby applied in insufficiency to the sample application zone 12. "In insufficiency" is to be understood, in this case, that the volume applied is smaller than the absorbent capacity of the sample application zone. Subsequently, the start zone is contacted with an elution agent, which is advantageously water or a buffer solution.

We have found that a dilution can thereby be achieved. The degree of the dilution can be influenced by the volume pipetted on to the sample application zone and the absorptive capacity of the start zone. An especial advantage of this method of handling is the fact that the samples can be dosed on at any desired point of time and allowed to dry, the elution and analyses then first taking place at a later point of time. In this way, series of test strips can be collected.

It is important for the dilution function of the sample application field that no enrichment of the sample disturbing the analysis occurs in the front of the chromatographing liquid. For this reason, it is advantageous to select for the sample application zone a material which fulfils this requirement on the basis of its particular properties. To these belong the following working principles:

a) The material is so chosen that the analyte pipetted on binds weakly on the solid phase and is retardedly eluted by the elution agent.

b) The material of the sample application zone is so structured that, by eddying and/or non-laminar flow, a mixing of the sample and elution agent is achieved.

Figure 2:
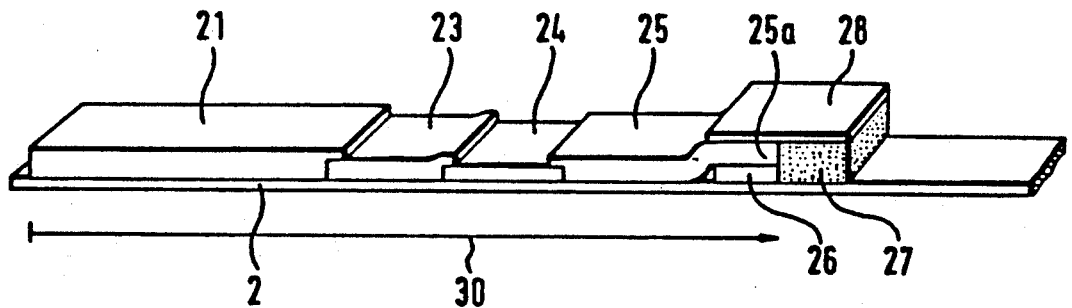
FIG. 2 is a perspective view of the test carrier.

FIG. 2 shows a test carrier which, in an especially simple way, permits the determination of comparatively highly dosed parameters with an immunoenzymometric test principle. It is especially suitable for the determination of such parameters in a sample liquid which is available in comparatively large amounts, especially in urine.

On a base layer 2 are arranged essentially next to one another a start zone 21, an auxiliary reagent zone 23, a conjugate zone 24 and a fixing zone 25. A colour-forming zone 26 is present between the end 25a of the fixing zone and the base layer. The end 25a of the fixing layer is thereby pressed by a holding-down layer 28 made from a stiff synthetic resin material against the colour-forming layer 26. The holding-down layer is fixed with a melt adhesive strip 27 to the base layer 2.

In FIG. 2, it can be seen that the layers 21 to 25 each overlap the neighbouring layer slightly in order to produce a better liquid contact on the edges of the zones. Essentially, however, the liquid transport takes place in the longitudinal direction of the test carrier and thus parallel to the surface of the layer materials from which the zones are produced, along the liquid transport path 30.

In use, the test carrier is dipped into the sample liquid to such an extent that only the start zone 21 is wetted. Thus, only the start zone makes contact with the sample liquid. Therefore, it must be such that it takes up the liquid spontaneously and completely and passes it on or gives it up well. For a test strip of the type here in question, it is important that all the zones placed after the start zone 21, which form the actual functional range of the test carrier, are supplied sufficiently and reproducably with liquid. This can be achieved by leaving the test carrier to stand in a vessel with the sample so that a continuous contact is present to a large supply of liquid. However, this makes the handling difficult. Therefore, it is desirable that the start zone 21 takes up a sufficient amount of liquid within a few seconds and, according to the test requirements, again gives it off after the test strip has been taken out of the sample liquid.

In contradistinction to the above-mentioned older suggestion according to European patent application No. 0,052,328, according to the present invention, the start zone consists of a nonswellable fibre fleece with a water-insoluble binding agent.

Especially preferred as non-swelling fibre materials are fully synthetic fibres. The fleece should contain at least 50% of such material. Polyamides and polyesters, as well as mixtures thereof, have proved to be especially useful.

As binding agent for the consolidation of the fibres, polyvinyl alcohol can advantageously be used. This takes place especially in such a manner that, in the production of the fleece, the actual fleece fibres are mixed in a vat with fibres of polyvinyl alcohol. They are then, as is usual in the case of the production of fleece, spread out on a drying roller. At a drying temperature of about 90° to 150° C., the polyvinyl alcohol fibres dissolve and form a coating on the other components of the fleece which imparts stability to the fleece. There is preferably used a high molecular weight, fully saponified polyvinyl alcohol with a specific weight of from 1.26 to 1.30 g./cm$^3$.

Especially preferred polyester fibres have a specific weight of about 1.17 g./cm$^3$, a length of cut of 6 to 12 mm. and a fibre fineness of 1.7 to 3.3 dtex.

Insofar as polyamide fibres are used, they preferably have a specific weight of about 1.14 to 1.15 g./cm$^3$, a length of cut of 4 to 6 mm. and a fibre fineness of 2.2 dtex.

As additional component, the fleece can contain linters from the base wool of the fibres obtained from cotton plants which have been chemically digested and bleached.

The further zones contain the same reagents as described in FIG. 1 for the case of an immunoenzymometric test. The auxiliary reagent zone 23 contains a buffer and optionally further adjuvant reagents, the conjugate zone 24 an enzyme conjugate of a (second) binding partner specifically bindable with the analyte, the fixing zone 25 solid-phase-bound analyte (or analyte analogue) and the colour-forming zone 26 a colour-forming substrate of the labelling enzyme.

For the determination of an antigen Ag, in the conjugate AbE zone 24 is used a conjugate of a corresponding antibody and in the fixing zone 25 the same antigen Ag or another antigen Ag* bindable with the antibody Ab of the layer 24. If an antibody is to be determined, then, as is known to the expert, in each case antigen is to be replaced by antibody.

Also in agreement with FIG. 1, a capturing reagent is provided, which is preferably soluble and identical with the enzymatically conjugated binding partner in the layer 24.

The course of the test corresponds to the immunoenzymometric variant of the test carrier according to FIG. 1 and, therefore, does not have to be described again here.

For the function of the test carrier according to FIG. 2, the liquid transport properties of the layer materials which form the different zones is of especial importance.

For an optimum accuracy of the test, it is necessary that the species characteristic for the analysis is present substantially homogeneously over the whole of the surface so that a homogeneous colour formation is obtained. Thus, in the case of an immunoenzymometric test, a homogeneous distribution of the Ag-AbE complexes is to be achieved in the colour-forming zone 26 characteristic for the analysis.

In the scope of the present invention, we have found that, in this sense, it is advantageous when the materials from which the conjugate zone and the next-following zone are produced have their absorbent properties so adjusted to one another that the material of the conjugate zone transports the liquid faster than the material of the next-following zone.

In the illustrated example, this refers to the conjugate zone 24 and the next-following zone 25 which, in the most general case, does not absolutely have to be a fixing zone. Since both zones lie in the same liquid stream, in the stationary state, when both zones are filled, they must transport the same amount of liquid per unit time. Slower flow of the liquid nevertheless results since the conjugate zone is thinner and therefore has a smaller flow cross-section than the next following zone.

This measure promotes the homogenisation of the conjugate. Depending upon the solution and liquid transport relationships of the conjugate zone 24, the conjugate is there dissolved by the entering liquid in the sense of a more or less sharp concentration front. This corresponds to the normal behaviour of an absorbent layer in liquid chromatography. It is the purpose of the here-discussed measure that the concentration differences resulting therefrom are to equalise. The conjugate zone is first filled comparatively fast, with little dissolving of the conjugate. The further liquid transport then follows comparatively slowly, corresponding to the liquid transport properties of the following zone. During this slow further flow, the conjugate already in the zone 24 dissolves comparatively homogeneously. Furthermore, the slow flow brings about an equilibrating effect within the zone 25.

In the case of the immunoenzymometric test, there is present, as explained, a fixing zone 25 behind the conjugate zone 24 and, in the most general case, further zones 24 can be present between the two zones 25. A preferred measure of the present invention provides that the fixing zone has a larger flow cross-section than the conjugate zone.

In the case of known immunological tests, there are preponderantly used fine-pore synthetic resin materials (membranes) of small thickness as fixing layer because they permit a high loading density of the carrier-fixed immunological reagents and the liquid flows slowly through them. A dependable fixing of the non-complexed conjugate from the preceding conjugate layer is thereby achieved. This is of great importance for the accuracy of the measurement.

Deviating from this previously known way, in the scope of the present invention, there is now preferably used a fixing layer which is produced on the basis of a comparatively loose carrier material, for example paper, fabric or especially preferably fleece. The layer material is relatively thick so that the fixing zone has a greater flow cross-section than the conjugate zone. In this way, there can here also be achieved a very high loading with immune reagents, in which case the production is considerably easier than in the case of a membrane. Due to the mentioned balancing of conjugate zone and fixing zone, there is given at the same time a comparatively slow flow in the fixing layer, which is of advantage for a complete binding of the excess conjugate.

The homogeneity of the colour formation in the layer 26 is, in the case of the illustrated test carrier, also promoted in that the colour-forming zone runs parallel to a part of the fixing zone and is in a laminar liquid contact with this. At the same time, the colour-forming zone is advantageously so formed that the liquid from the fixing zone 25 only penetrates retardedly into it or the substrate in the zone 26 dissolves retardedly in such a way that the fixing zone 25 has filled substantially completely before the colour-forming reaction commences. In this regard, reference is made to Federal Republic of Germany patent application Nos. P 38 26 056.5 and P 38 26 057.3 of the 30th Jul., 1988. These applications correspond to respective U.S. application Ser. Nos. 384,982 and 384,726.

The following Examples are given for the purpose of illustrating the present invention:

EXAMPLE 1

Water Take-Up and Output Properties of Materials Suitable for the Start Zone 11,21

A swelling sponge material according to European patent application No. 0,052,328 was compared with the following three materials according to the present invention:

a) Mixed Fleece of Polyamide and Polyester

The materials were mixed in a vat together with Kuralon (polyvinyl alcohol produced by Rohtex-Textil, Mönchengladbach, Federal Republic of Germany) in a weight ratio of polyamide:polyester:Kuralon of 30:20:2.6 and worked up in known manner to give a fleece with a weight per unit surface area of 160 g./m$^2$ and a thickness of 1.0 mm.

b) Pure Polyester Fleece

Polyester and Kuralon were mixed in a vat in a weight ratio of 10:1 and worked up to give a fleece with a weight per unit surface area of 166 g./m$^2$ and a thickness of 1.0 mm.

c) Polyester Fleece with Linters

Polyester, linters and Kuralon were mixed in a vat in a weight ratio of 50:25:7.5 and worked up to give a fleece with a weight per unit surface area of 250 g./m$^2$ and a thickness of 1.4 mm.

The following Table shows the retention behaviour of such fleece:

TABLE

| | water take-up | water output | retention |
|---|---|---|---|
| sponge according to EP 0,052,328 | 5632 ml/m$^2$ | 3862 ml/m$^2$ | 31.4% |
| fleece a) | 1825 ml/m$^2$ | 1636 ml/m$^2$ | 10.4% |
| fleece b) | 1751 ml/m$^2$ | 1568 ml/m$^2$ | 10.5% |
| fleece c) | 1866 ml/m$^2$ | 1548 ml/m$^2$ | 17.1% |

It can be seen that the water take-up is the highest in the case of the previously known sponge. The same also applies to the water output. However, of especial importance for the function of the test carrier is the retention, i.e. the percentage of the liquid remaining behind in the particular test zone under certain defined experimental conditions. From the example, it can be seen that this value is, in the case of all three compositions according to the present invention, considerably better than in the case of the previously known start zone material.

EXAMPLE 2

Test Carrier for the Determination of Albumin in Urine and Especially for the Detection of Microalbuminuria A test carrier according to FIG. 2 was produced as follows:

Start Zone 11

Polyester fleece 1.110 of the firm Binzer, Hatzfeld, Federal Republic of Germany. It is a pure polyester fleece consolidated with 10% Kuralon. The thickness is 1.0 to 1.2 mm and absorption capacity 1800 ml./m$^2$.

Buffer Zone 23

A fleece material SL 4207 KA of the firm Kalff, Euskirchen, Federal Republic of Germany, consisting of 90% polyester, 10% regenerated cellulose and a small amount of acrylate, with a thickness of 0.7 mm. and an absorptive capacity of 480 ml./m$^2$, was impregnated with the following solution and subsequently dried:

200 mM sodium phosphate, pH 7.8
1% bovine serum albumin.

Conjugate Zone 24

A glass fibre fleece of 100 parts by weight of glass fibre, consolidated with 10 parts by weight of Kuralon, in a thickness of 0.2 mm. and with an absorption capacity of 200 ml./m$^2$, was impregnated with the following solution and subsequently dried:

70 mM sodium phosphate, pH 7.4
1% trehalose
0.5% bovine serum albumin
6 kU/liter conjugate of $\beta$-galactosidase and analyte-specific antibody (IgG)
70 mg./l unlabelled analyte-specific antibody (IgG) as capturing reagent.

Fixing Zone 25

A mixed fleece of polyester, cotton linters and Etadurin ® in a weight ratio of 50:50:3 with a thickness of 0.5 mm. and an absorption capacity of 450 ml./m$^2$ was impregnated with the following solution and subsequently dried for 30 minutes at 50° C. 10 mM sodium phosphate buffer, pH 7.5 cross-linked human serum albumin in a concentration of 200 mg./ml. sodium phosphate buffer The cross-linked human serum albumin was prepared as follows:

1.5 g Human serum albumin was placed in 30 ml. of 200 mM potassium phosphate buffer (pH 8.0) and mixed within the course of 2 hours with 2.5 ml. of a solution of 50 mg. disuccinyl suberate/ml. dioxan. After termination of the cross-linking reaction, dialysis was carried out against a 500 fold volume of 20 mM potassium phosphate buffer (pH 7.2). The high molecular weight fraction with a molecular weight of more than 650,000 Dalton was separated on Superose 6 ® (Pharmacia, Freiburg, Federal Republic of Germany) by gel filtration and, after the addition of 6 mg. saccharose/mg. protein, lyophilised.

Colour-Forming Zone 26

On a polycarbonate film of 0.1 mm. thickness was coated a soluble film of the following formulation:

4.5 g Mowiol 18/88 (firm Hoechst, Frankfurt am Main, Federal Republic of Germany)
0.3 g o-nitrophenol-$\beta$-galactoside dissolved in 50 ml. water.

We claim:

1. Test carrier for analysis of a sample liquid by means of a binding reaction between a first binding partner contained in the sample and a second binding partner contained in the test carrier, said reaction leading to a labelled species characteristic of the desired analysis, said test carrier comprising a base layer,
a plurality of capillary action test zones arranged on said base layer in liquid contact with one another so as to form a liquid transport path parallel to said base layer, said zones comprising, in order, a sample application zone to which said sample liquid including a first specific binding partner is applied, a conjugate zone containing a labelled conjugate of one of said first and a second specific binding partners, and a detection zone containing a carrier fixed specific binding partner selected from the group consisting of the other of said first and second specific binding partners and a further specific binding partner which binds with said first specific binding partner, said reaction occurring in one of said conjugate zone and said detection zone, said labelled species being detected in said detection zone, and a third specific binding partner which specifically binds with said first binding partner, said third binding partner being contained in one of said conjugate zone and a zone between said sample application zone and said conjugate zone, said third binding partner being so measured that it binds only a part of the first binding partner, thereby acting as a capturing reagent which removes said part from the reaction leading to the characteristic labelled species.

2. Test carrier according to claim 1, wherein the capturing reagent is soluble in the sample liquid.

3. Test carrier according to claim 1, wherein said conjugate is a labelled conjugate of the second binding partner and is soluble in the sample liquid.

4. Test carrier according to claim 3, wherein the capturing reagent is arranged in the conjugate zone.

5. Test carrier according to claim 3, wherein the conjugate zone has a smaller flow cross-section than the next following zone in the liquid transport path.

6. Test carrier according to claim 3 further comprising a fixing zone in the liquid transport path after the conjugate zone, which fixing zone contains, in carrier-fixed form, a binding partner of the second binding partner which binds to the second binding partner in a manner analogous to the binding of the first binding partner to the second binding partner.

7. Test carrier according to claim 6, wherein the fixing zone has a larger flow cross-section than the conjugate zone.

8. Test carrier according to claim 1 further comprising an auxiliary reagent zone in which the capturing reagent is carrier-fixed in the liquid transport path between the sample application zone and the conjugate zone.

9. Test carrier according to claim 1, wherein the second binding partner and the third binding partner are the same.

10. Test carrier as in claim 1 wherein said labelled conjugate is a conjugate of said first binding partner, said second binding partner being carrier-fixed in the liquid transport path after said conjugate zone, whereby said first binding partner and said labelled conjugate compete for binding to said second binding partner.

11. Test carrier as in claim 1 further comprising a start layer in said sample application zone, said start layer having the capacity to take up sufficient liquid to fill the entire liquid transport path and to pass said liquid into said zones forming said transport path.

12. Test carrier as in claim 11 wherein said start layer comprises a non-swelling fiber fleece bound with a binding agent which is insoluble in the sample liquid.

13. Test carrier as in claim 11 wherein said start zone comprises a non-swelling fiber fleece with a water-soluble binding agent.

14. Test carrier for the analytical investigation of a sample liquid by means of an analysis reaction which includes a specific binding reaction of a first specific binding partner which is contained in the sample and a second specific binding partner which is contained in the test carrier and leads to a labelled species characteristic for the desired analysis, comprising a plurality of capillary action test zones arranged next to one another on a base layer and in liquid contact with one another so as to form a liquid transport path parallel to the base layer along which a liquid flows driven by capillary forces for performing said analysis reaction, said capillary action test zones including, in order, a sample application zone to which said sample liquid including a first specific binding partner is applied, a conjugate zone containing a labelled conjugate of one of said first and a second specific binding partners, and a detection zone, containing a carrier fixed specific binding partner selected from the group consisting of the other of said first and second specific binding partners and a further specific binding partner which binds with said first specific binding partner, said reaction occurring in one of said conjugate zone and said detection zone, said labelled species being detected in said detection zone, said capillary action test zones comprising a first zone in said transport path, said first zone comprising a start layer for dipping into a sample liquid to spontaneously take up sufficient liquid in order to fill the whole of the liquid transport path and for passing on said liquid into remaining said zones forming said liquid transport path, said start layer being made of a non-swelling fiber fleece with a binding agent insoluble in said sample liquid.

15. Test carrier according to claim 14, wherein the fibre fleece has a retention for the sample liquid of at most 25%.

16. Test carrier according to claim 15, wherein the fibre fleece contains at least 50% of synthetic fibres.

17. Test carrier according to claim 16, wherein the synthetic fibres are polyamide or polyester fibres.

18. Test carrier according to claim 16 wherein the fiber fleece contains polyvinyl alcohol.

* * * * *

UNITED STATES PATENT AND TRADEMARK OFFICE
CERTIFICATE OF CORRECTION

PATENT NO. : 5,160,486
DATED : November 3, 1992
INVENTOR(S) : Reiner Schlipfenbacher et al.

It is certified that error appears in the above-indentified patent and that said Letters Patent is hereby corrected as shown below:

Column 4, line 36, delete "contact" and insert -- contacted --.

Column 5, line 45, delete "AbL(f)" and insert -- Ab1(f) --.

Signed and Sealed this

Twenty-ninth Day of March, 1994

Attest:

BRUCE LEHMAN

*Attesting Officer*    Commissioner of Patents and Trademarks